(12) United States Patent
Levy

(10) Patent No.: US 7,104,794 B2
(45) Date of Patent: Sep. 12, 2006

(54) ULTRASONIC DENTAL TOOL HAVING A LIGHT SOURCE

(75) Inventor: Haim Levy, Hod Hasaron (IL)

(73) Assignee: Discus Dental Impressions, Inc., Culver City, CA (US)

( * ) Notice: Subject to any disclaimer, the term of this patent is extended or adjusted under 35 U.S.C. 154(b) by 0 days.

(21) Appl. No.: 10/879,554

(22) Filed: Jun. 28, 2004

(65) Prior Publication Data

US 2005/0032017 A1    Feb. 10, 2005

Related U.S. Application Data

(60) Provisional application No. 60/482,717, filed on Jun. 27, 2003.

(51) Int. Cl.
*A61C 3/01* (2006.01)
*A61C 1/07* (2006.01)
(52) U.S. Cl. .......................... 433/29; 433/119
(58) Field of Classification Search ............... 433/29, 433/118, 119
See application file for complete search history.

(56) References Cited

U.S. PATENT DOCUMENTS

| | | |
|---|---|---|
| 3,109,238 A | 11/1963 | Marks |
| 3,731,384 A | 5/1973 | Brooks et al. |
| 3,789,506 A | 2/1974 | Johns |
| 4,375,964 A | 3/1983 | Knopp et al. |
| 4,518,355 A | 5/1985 | Hoffmeister et al. |
| 4,634,376 A | 1/1987 | Mössle et al. |
| 4,642,738 A | 2/1987 | Meller |
| 4,790,751 A | 12/1988 | Reinhardt et al. |
| 4,840,563 A | 6/1989 | Altendorf |
| 4,983,121 A | 1/1991 | Straihammer et al. |
| 5,281,134 A | 1/1994 | Schultz |
| 5,655,906 A * | 8/1997 | Coss et al. ............... 433/115 |
| 5,683,246 A | 11/1997 | Coss et al. |
| 5,800,172 A | 9/1998 | Goldenberg |
| 5,908,295 A | 6/1999 | Kawata |
| 6,059,810 A | 5/2000 | Brown et al. |
| 6,095,810 A | 8/2000 | Bianchetti |

(Continued)

FOREIGN PATENT DOCUMENTS

DE    3422628    12/1985

(Continued)

OTHER PUBLICATIONS

PCT Search Report; dated Sep. 12, 2005; for Application No. PCT/US04/20804; in the name of Discus Dental Impressions, Inc.

*Primary Examiner*—Cary E. O'Connor
(74) *Attorney, Agent, or Firm*—Christie, Parker & Hale, LLP.

(57) ABSTRACT

An ultrasonic dental insert having at least one light source. A first transducer generates ultrasonic vibrations. A connecting body has a proximal end and a distal end having a tip attached thereto. The proximal end is attached to the first transducer so as to receive the ultrasonic vibrations therefrom and to transmit the ultrasonic vibrations toward the tip attached to the distal end. A second transducer is disposed substantially proximate to the connecting body for generating a voltage signal in response to movement of a portion of the connecting body according to the ultrasonic vibrations. At least one light source substantially proximate to the tip is connected to and receives the voltage signal from the second transducer to generate light. The ultrasonic dental insert may be inserted into a handpiece for providing electromagnetic energy to the first transducer to generate the ultrasonic vibrations.

59 Claims, 11 Drawing Sheets

U.S. PATENT DOCUMENTS

| | | | |
|---|---|---|---|
| 6,386,866 B1 * | 5/2002 | Hecht et al. | 433/29 |
| 6,561,801 B1 | 5/2003 | Nakanishi | |
| 2003/0108844 A1 * | 6/2003 | Rahman et al. | 433/119 |

FOREIGN PATENT DOCUMENTS

| | | |
|---|---|---|
| DE | 3706943 | 9/1988 |
| FR | 2687060 | 8/1993 |
| JP | 05031124 A | 2/1993 |
| JP | 07275261 A | 10/1995 |

* cited by examiner

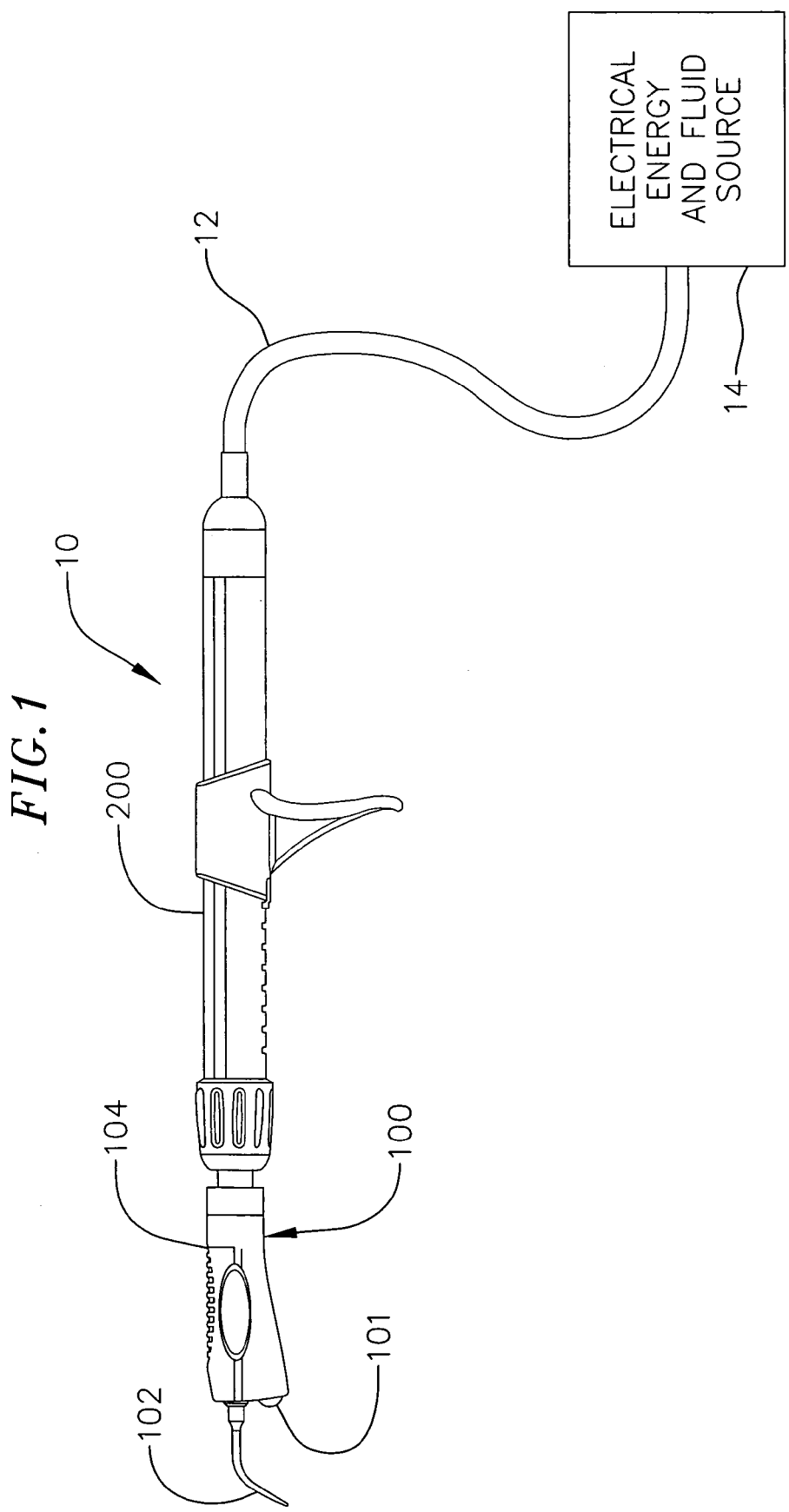

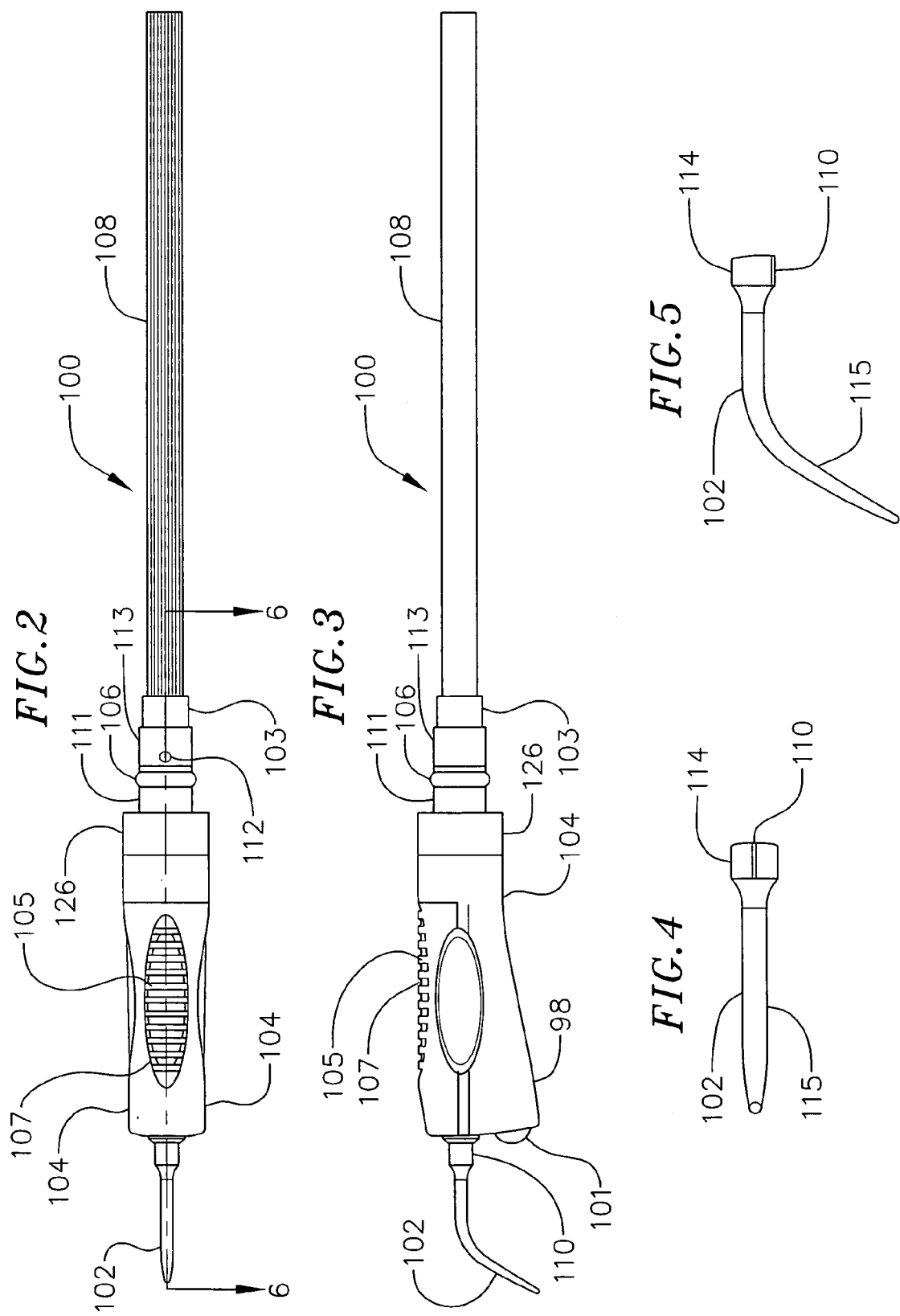

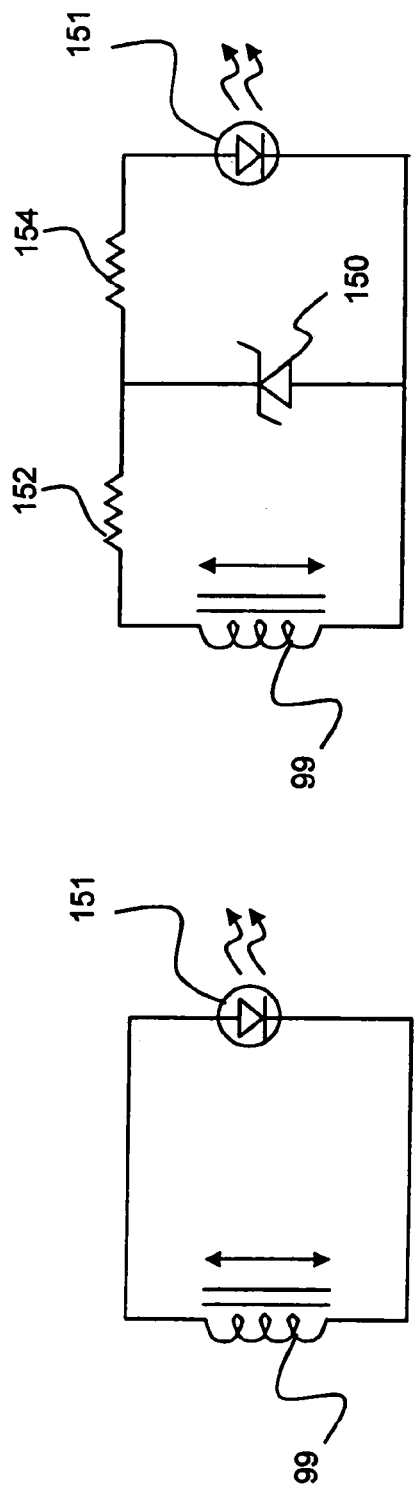
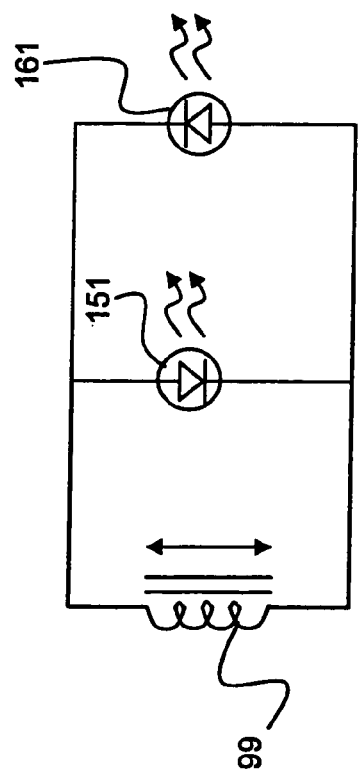

ULTRASONIC DENTAL TOOL HAVING A LIGHT SOURCE

CROSS-REFERENCE TO RELATED APPLICATIONS

This application claims the benefit of U.S. Provisional Patent Application No. 60/482,717 entitled "Ultrasonic Dental Tool with Disposable Lighted Tip" filed Jun. 27, 2003, the entire content of which is incorporated herein by reference. This application contains subject matter related to the subject matter disclosed in U.S. patent application Ser. No. 10/735,147 entitled "Ultrasonic Dental Insert Having Interchangeable Plastic and Metal Tips", U.S. patent application Ser. No. 10/735,050 entitled "Ultrasonic Dental Handpiece Having a Rotatable Head" and U.S. patent application Ser. No. 10/734,517 entitled "Ultrasonic Dental Insert Having a Hand Grip Fitted to a Retaining Ring," all filed Dec. 12, 2003, the entire contents of all three of which are incorporated by reference herein.

FIELD OF THE INVENTION

The present invention is related to ultrasonic dental tools, and more particularly to an ultrasonic dental tool having a light source.

BACKGROUND

Dental practitioners use ultrasonic dental tools (instruments) for dental treatments and procedures, such as scaling, periodontal treatments, root canal therapy, and the like. An ultrasonic dental tool typically includes a handpiece coupled at one end (i.e., a proximal end) to an electrical energy source and a fluid source via a cable. The cable includes a hose to provide a fluid (e.g., water), and conductors to provide electrical energy.

The other end (i.e., a distal end) of the handpiece has an opening intended to receive a replaceable insert with a transducer (e.g., a magnetostrictive transducer) carried on the insert. The transducer extends from a proximal end of the insert into a hollow interior of the handpiece. An ultrasonically vibrated tip extends from a distal end of the insert.

Since a mouth is a small space in which to work, it is often difficult to see well into all regions of the mouth under the best of conditions. When a dental practitioner cannot see clearly in the field of work, it is more likely that painful slips can occur. The often sharp implements, vibrating at ultrasonic frequencies, can do considerable harm to soft tissue (such as gum tissue) resulting in bleeding and pain.

The large and focused lamp that hangs over the field of work while the dental practitioner uses ultrasonic dental tools in the patient's mouth often becomes obscured when the dental practitioner leans closely toward the patient to work in confined spaces within the mouth. The suddenly darker field is more difficult in which to work accurately. Small slips and injuries can result.

Therefore, it is desirable to provide an ultrasonic dental tool that can bring light directly into the field of work (i.e., patient's mouth). If such light can be provided using a source of energy already available in existing ultrasonic dental tools, circuit complexity and energy requirements can be reduced.

SUMMARY

In an exemplary embodiment of the present invention, an ultrasonic dental insert has at least one light source. The ultrasonic dental insert includes a first transducer for generating ultrasonic vibrations. The ultrasonic dental insert also includes a connecting body having a proximal end and a distal end having a tip attached thereto. The proximal end is attached to the first transducer so as to receive the ultrasonic vibrations therefrom and to transmit the ultrasonic vibrations toward the tip attached to the distal end.

A second transducer is disposed on the insert, substantially proximate to the connecting body and generates a voltage signal in response to movement of a portion of the connecting body according to the ultrasonic vibrations. At least one light source substantially proximate to the tip is connected to and receives the voltage signal from the second transducer to generate light.

The ultrasonic dental insert may be inserted into a handpiece for providing electromagnetic energy to the first transducer to generate the ultrasonic vibrations, to form an ultrasonic dental tool having a light source.

In another exemplary embodiment of the present invention, a method of generating light used during dental procedures is provided. Ultrasonic vibrations are generated using a first transducer attached to a proximal end of a connecting body having a proximal end and a distal end having a tip attached thereto. The ultrasonic vibrations are transmitted through the connecting body toward the tip attached to the distal end of the connecting body. A voltage signal is generated using a second transducer disposed along the insert, substantially proximate to the connecting body in response to the movement of a portion of the connecting body according to the ultrasonic vibrations. The light is emitted from at least one light source substantially proximate to the tip and connected to the second transducer using the voltage signal.

In yet another exemplary embodiment of the present invention, a method of illuminating a work region is provided. Mechanical energy is received at a generator, said generator being mechanically supported by a tool handle, said tool handle being adapted to support an ultrasonic tool tip. The mechanical energy is converted to electromagnetic energy, and a work region is illuminated using at least a portion of said electromagnetic energy.

In still another exemplary embodiment of the present invention, a method of cleaning a tooth surface is provided. An ultrasonic signal is received at a dental tool handpiece. The ultrasonic signal is converted to an ultrasonic motion of a connecting body supporting a dental tool tip. The ultrasonic motion of said connecting body is coupled to an electrical generator. An electrical current is generated with said electrical generator. At least one light source is energized with said electrical current. The dental tool tip is contacted to a surface of a tooth. The surface of a tooth adjacent said dental tool tip is illuminated with said light source.

In a still further exemplary embodiment of the present invention, an ultrasonic dental insert is provided. The ultrasonic dental insert includes a motor, a work tip, and a coupling member disposed between said motor and said work tip, said coupling member being adapted to receive mechanical energy from said motor. An electrical generator is mechanically coupled to said coupling member, said electrical generator being adapted to receive a portion of said mechanical energy from said coupling member. An electrical conductor has a first end electrically coupled to said electrical generator. At least one light source has an electrical input electrically coupled to a second end of said electrical conductor.

BRIEF DESCRIPTION OF THE DRAWINGS

These and other aspects of the invention may be understood by reference to the following detailed description, taken in conjunction with the accompanying drawings, wherein:

FIG. 1 illustrates an ultrasonic dental unit (or system) including an ultrasonic dental tool attached to an electrical energy & fluid source;

FIG. 2 is a top view of a dental tool insert having an integrated light source in an exemplary embodiment of the present invention;

FIG. 3 is a side view of the dental tool insert of FIG. 2, which has been rotated by approximately 90 degrees from the top view depicted in FIG. 2;

FIG. 4 illustrates a tip for the dental tool insert of FIG. 2;

FIG. 5 illustrates the tip of FIG. 4, which has been rotated by approximately 90 degrees;

FIGS. 8, 9 and 10 illustrate light emitting circuitry of the integrated light source in exemplary embodiments of the present invention;

DETAILED DESCRIPTION

Figure 6A:
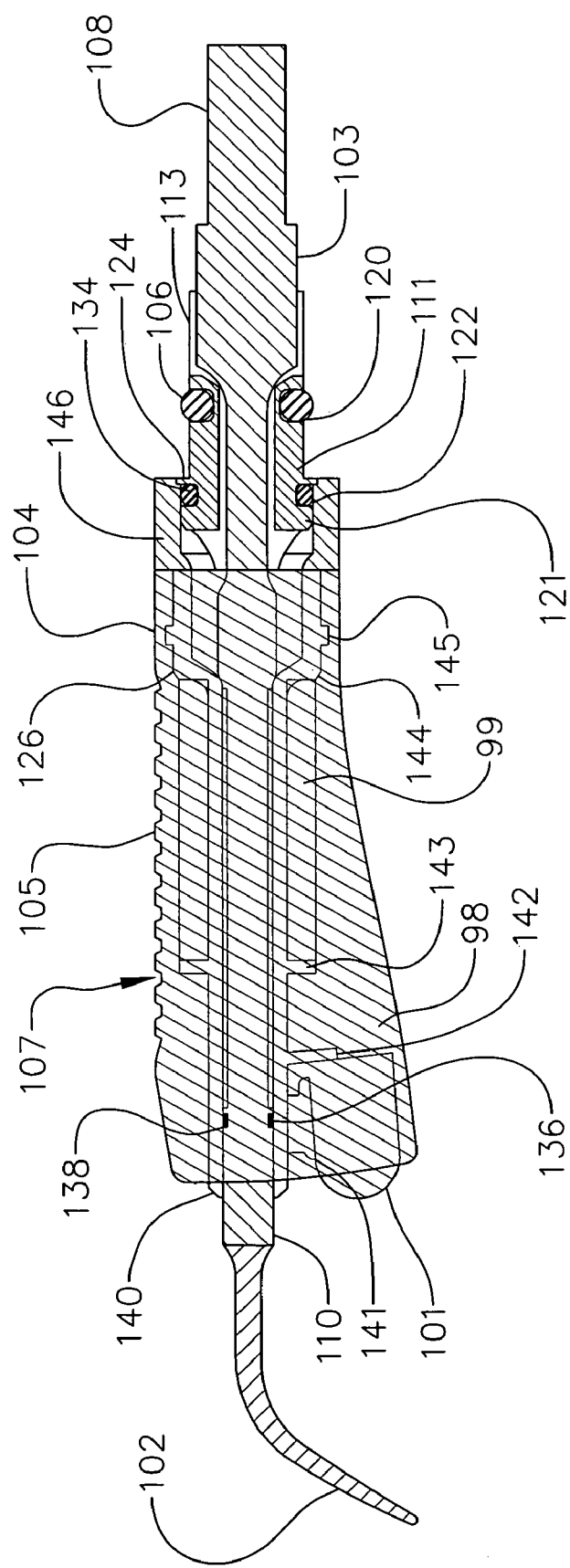
FIG. 6A is a cross-sectional view of the dental tool insert of FIG. 2, taken along the line 6—6.

In exemplary embodiments of the present invention, an ultrasonic dental insert has at least one integrated light source such as a light emitting diode (LED) that enables a dental practitioner to cast light on the work field while applying a tool to the teeth. The light source is energized by the already available ultrasonic vibrational energy such that an additional source of energy is not needed. By way of example, a transducer such as and/or including an illumination energy coil is provided and attached to the light source such that the light source is energized using vibrational energy converted by the transducer. By way of example, as the connecting body of the dental insert moves rapidly, an alternating current (ac) voltage is generated in the illumination energy coil, which is connected in series with the light source (e.g., light emitting diode (LED)) to provide energy for light emission. In other embodiments, any other suitable transducer for converting vibrational energy to an energy for light emission may be used. The word "light source" as used herein can include one or more than one light source(s).

FIG. 1 illustrates an ultrasonic dental unit including an ultrasonic dental tool 10 attached to an electrical energy & fluid source 14 via a cable 12. The cable 12 includes a conduit for carrying fluid as well as wires for carrying electrical signals from the electrical energy & fluid source 14 to the ultrasonic dental tool 10. The ultrasonic dental tool 10 includes a handpiece 200 and an insert 100 inserted into the handpiece 200. It can be seen in FIG. 1 that a light source 101 has been integrated with the insert 100 near its distal end, substantially proximate to a tip 102. In another embodiment, a plurality of light sources are integrated with the insert 100 near the distal end. In other embodiments, the light source may include two or more lights (such as LEDs 151 and 161 shown in FIG. 10). In still other embodiments, the light source may not be integrated with the insert, but may instead be non-integrally attached to the insert and/or the hand grip, or only one light source is integrated with the insert and additional ones are not.

Referring now to FIGS. 2 and 3, the dental insert 100 includes the tip 102 at its distal end and an ultrasonic transducer 108 at its proximal end. The tip 102 is coupled to the transducer 108 via a connecting body 103, which may take the form of a shaft. The tip 102 may be removably attached to the connecting body 103 so that tips can be interchanged depending on the desired application. Further, the tip 102, when removed, may be disposed or steam autoclaved, or otherwise sterilized, after detaching it from the rest of the ultrasonic dental insert. For example, the tip 102 may be made using high temperature plastic such as ULTEM®, which is an amorphous thermoplastic polyetherimide or Xenoy® resin, which is a composite of polycarbonate and polybutyleneterephthalate or Lexan® plastic, which is a copolymer of polycarbonate and isophthalate terephthalate resorcinol resin, all available from GE Plastics, or any other suitable resin plastic or composite. The tip may also be made of metal or metallic alloys such as stainless steel. The term "plastic" is used herein to generally designate synthetic polymeric material, such as resin.

The connecting body is made of material suitable for transmitting ultrasonic vibrations such as stainless steel. The connecting body is used to deliver ultrasonic vibrations generated by the transducer 108 to the tip 102. The transducer 108, for example, may be attached to the connecting body 103 by soldering, welding, laser welding and/or any other suitable method. For example, the joint between the connecting body 103 and the transducer 108 may be a brazed joint formed using a brazing compound, which includes cadmium free silver solder and high temperature brazing flux.

When the connecting body is also used to generate voltage in an illumination energy coil surrounding at least a portion of the connecting body, the connecting body is preferably made of a material that has magnetic permeability, preferably good magnetic permeability. By way of example, 17-4 PH stainless steel while suitable for transmitting ultrasonic vibrations, is also mildly magnetic. Therefore, the connecting body formed from 17-4 PH stainless steel will generate an ac voltage on the illumination energy coil by moving rapidly (e.g., 25 kHz or faster) within the illumination energy coil, which is mounted on an illumination energy bobbin 126. While only an end of the illumination energy bobbin 126 is shown in FIGS. 2 and 3, the illumination energy bobbin 126 actually envelops much of the connecting body 103 in the described embodiment as will be discussed in reference to FIGS. 6 and 7.

The connecting body 103 has mounted thereon an annular retaining ring 111, which may also be made of metal such as stainless steel. The retaining ring 111 has a connecting portion 113, which has a generally cylindrical cavity formed therein for receiving a corresponding portion of the connecting body 103 in a force-fit relationship. The retaining ring is fixedly attached (e.g., snapped on) to the connecting body 103 such that it neither rotates nor moves laterally along the axis of the connecting body.

The ultrasonic dental insert 100 also includes the hand grip 104, which may be made of high temperature resin. For example, the hand grip 104 may be fabricated using thermoplastic elastomer such as SANTOPRENE® available from the Monsanto Company, or those used in the construction of some tips, or any other suitable material. The hand grip 104 may be formed through injection molding after mounting the illumination energy coil and the light source 101 on the connecting body 103 via the illumination energy bobbin 126.

In other embodiments, the hand grip 104 may be a one-piece hand grip, which is mounted on the illumination energy bobbin 126 having a surrounding relationship with the connecting body 103 by sliding it over the illumination energy bobbin 126. In still other embodiments, multi-piece hand grips may be used. By way of example, a two-piece handgrip may be ultrasonically welded together over the illumination energy bobbin 126. The one-piece or two-piece hand grip may be made of ULTEM®, SANTOPRENE®, Xenoy® or Lexan® or other suitable resin plastic, for example.

The hand grip 104 has a generally cylindrical shape, and is fitted over the illumination energy bobbin 126 and secured in place (e.g., through injection molding directly on the illumination energy bobbin 126). The hand grip 104 also has a slightly protruding portion 98 on one side at the end of which the light source 101 (e.g., LED) is disposed. In other embodiments, the retaining ring 111 may not be used.

Along its outer surface on the other side of the slightly protruding portion 98, the hand grip 104 has a contour and has a slightly concave area 107, enabling it to be easily grasped by a dental practitioner. The hand grip 104 also has formed thereon a plurality of bumps 105 (i.e., striped protrusions as shown in FIG. 2) on its external surface to further facilitate grasping of the device by a dental practitioner. Some may even be ergonomically designed. In the described embodiment, a linear groove (e.g., a passageway) 110 is formed on the tip 102 for delivering fluid (e.g., water) and/or air to the gum or tooth of the patient.

The tip can be in the form of a scaler, an endodontic dental file, a drill, or those useful for other periodontal treatments. The tip can also be made of metal or plastic, as discussed above. Some of them can also have a capability of delivering fluid and/or air.

The retaining ring 111 has an opening 112 formed thereon for receiving fluid from the handpiece 200. The fluid may exit through the linear groove 110 formed on the base of the tip 102. In other embodiments, the insert may have an opening at the end of its tip 102 or an external tube for enabling the fluid to exit the insert. Further, an opening for applying the fluid to the mouth may instead be formed on the bobbin or the hand grip.

Figure 12:
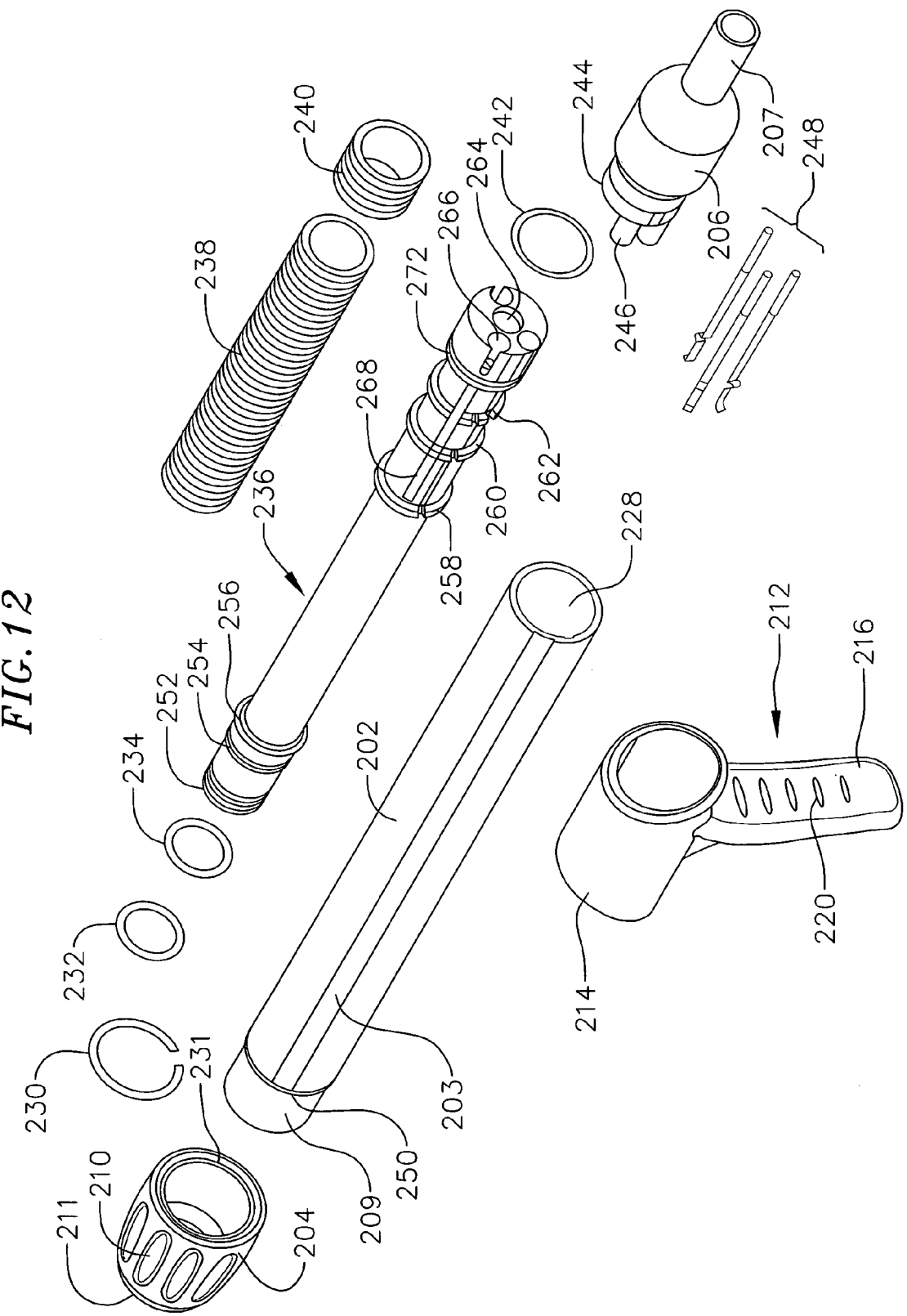
FIG. 12 is an exploded perspective view of the ultrasonic dental handpiece of FIG. 11.

The transducer 108 may, for example, include a stack of thin nickel plates arranged in parallel with respect to one another. Since the transducer 108 generates the ultrasonic vibrations in the dental tool, the transducer 108 may also be referred to as a motor. In one embodiment the thin nickel plates may include 16 laminated nickel alloy strips, which are 90% nickel manganese (NiMn). The nickel plates may be joined together at both ends at a brazed joint using, for example, a brazing compound including cadmium free silver solder and high temperature brazing flux. The illustrated insert 100 is a magnetostrictive type insert in which the nickel plates 108 can vibrate ultrasonically when a coil (e.g., coil 238, as shown in FIG. 12) in the handpiece is energized using the electrical signals from the cable. In other embodiments, the ultrasonic dental insert may use a piezoelectric transducer, as is common in Europe.

The insert 100 has an O-ring 106 mounted thereon for engaging and pressing against the inner surface of the handpiece 200 so as to form a water tight seal. For handpieces having a rotatable rotator head, the O-ring 106 may engage the rotator head such that the ultrasonic dental insert rotates together with the rotator head.

During operation, the stack of thin nickel plates 108 vibrates at a frequency equal to the stack's natural frequency responsive to excitation induced by coils of the handpiece 200. After the insert is placed in the handpiece and the electrical energy source is powered on, the operator manually tunes the frequency of the electrical energy source until it reaches the resonance frequency, i.e., the natural frequency of the insert. Alternatively, auto-tune units may automatically lock on the insert resonance frequency once powered on. At this time, the stack begins vibrating. This vibration of the stack is amplified and transmitted to the tip 102 through the connecting body 103. Any means of amplification are contemplated. Ultrasonic inserts used in the United States are typically designed to vibrate at 25 kHz or 30 kHz frequencies.

In response to the ultrasonic vibration of the stack of thin nickel plates 108, the tip of the connecting body vibrates (e.g., rapid back and forth motion in the direction of the axis of the connecting body 103). By way of example, the motion in the direction of the axis may be between 0.00125 centimeter (cm) to 0.00375 cm depending on such factors as the vibration frequency, material used for the connecting body 103, the length of the connecting body 103, and the like.

Referring now to FIGS. 4 and 5, the tip has an elongated tapered portion 115, and a cylindrical interface portion 114 ("base"). It can be seen in FIG. 5 that the tapered portion 115 is curved. The tapered portion 115 has a circular cross section whose diameter decreases gradually from the end abutting the interface portion 114 ("the proximal end") to the other end of the tip ("the distal end"). The distal end is applied to the gum/teeth of the patient during the dental procedures.

It can be seen in FIG. 4, that the cylindrical interface portion 114 has the linear groove 110 formed in the direction of the axis of the insert 100. The fluid traveling through the illumination energy bobbin 126 exits through the linear groove 110 in the described embodiment. In other embodiments, the tip may have a small passageway therethrough for supplying water or other fluid to the region in the mouth being operated on.

The tip 102 may be formed as a single integrated piece with the connecting body 103. In other embodiments, the tip may have attached to the interface portion a threaded portion for engaging a threaded opening formed on the connecting body (as shown in FIG. 6B). Using such threaded engagement, the tip may be made removable. Such removability would allow the tip to be a disposable tip that is replaced after a single patient use. In still other embodiments, the removable tips may also be pressure fit into a corresponding opening on the connecting body.

Figure 6B:
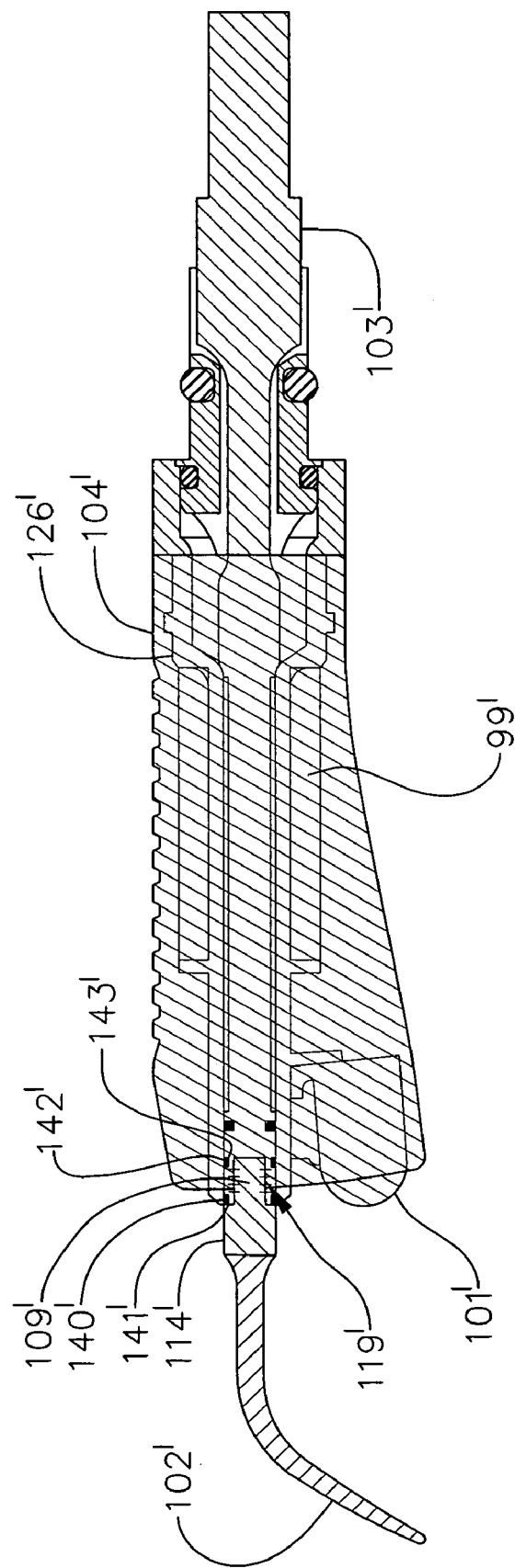
FIG. 6B is a partial cross-sectional view of the dental tool insert in another exemplary embodiment of the present invention.
Figure 7:
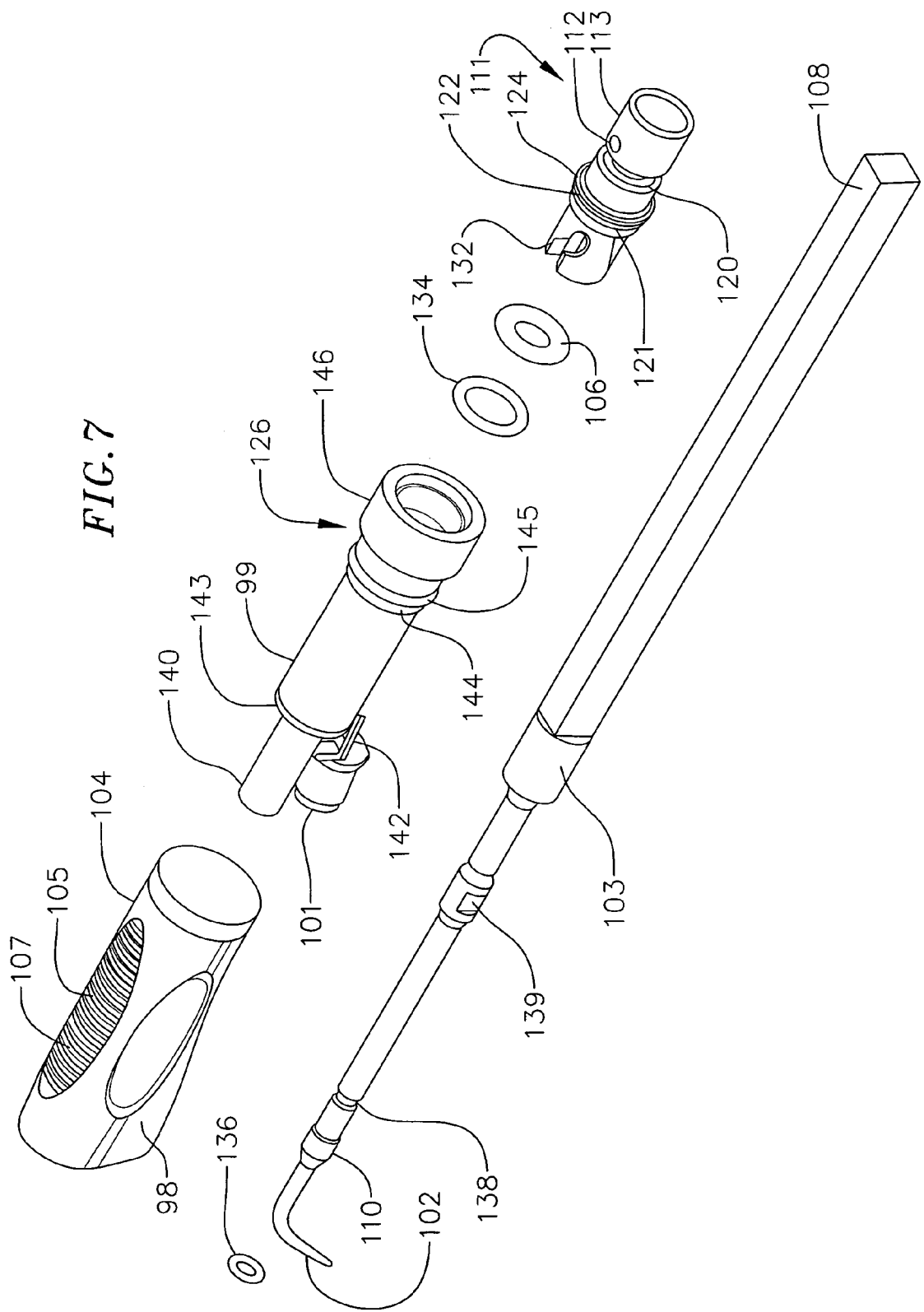
FIG. 7 is an exploded perspective view of the dental tool insert of FIG. 2.

Referring now to FIGS. 6A and 7, the connecting body 103 has also formed thereon a circular groove 138 near its distal end. An O-ring 136 is seated in the groove 138. When the illumination energy bobbin 126 is mounted on the connecting body 103, the O-ring 136 provides a seal between the connecting body 103 and the illumination energy bobbin 126 so as to prevent undesired fluid leakage.

The illumination energy bobbin 126 may be formed as one-piece, and may be slid onto and snap/pressure fit to the connecting body and/or the retaining ring 111.

The retaining ring 111 has a generally cylindrical shape, and has formed thereon a connecting portion 113 fitting over a corresponding cylindrical portion of the connecting body 103. Two openings 112 for receiving fluid from the handpiece are formed on opposite sides of the connecting portion 113. The retaining ring 111 has formed thereon, adjacent to the connecting portion 113, a circular groove 120 for seating the external O-ring 106.

At the distal end, the retaining ring 111 has formed thereon a pair of gripping elements 132 that face each other. Each gripping element has an end portion that protrudes inwardly toward the end portion of the other gripping element. The connecting body 103 has a pair of indentations 139 formed thereon for receiving the protruding end portions of the gripping elements such that the gripping elements 132 are snapped into the indentations 139. Thus engaged, the retaining ring 111 of the illustrated embodiment is locked to the connecting body 103, and neither rotates nor moves laterally with respect to the same. The retaining ring 111 has also formed thereon circular flanges 121, 124 and a circular groove 122. The circular groove 122 is for seating an O-ring 134.

It can be seen in FIGS. 6A and 7 that the illumination energy coil 99 is wound around the illumination energy bobbin 126, which is mounted in a surrounding relationship with the connecting body 103. The bobbin 126, for example, may be made of high temperature plastic such as ULTEM® or any other suitable material. The amount of voltage generated in the illumination energy coil 99 depends on such factors as the number of coil turns, the location of the illumination energy coil 99 with respect to the connecting body 103, the speed and frequency of the connecting body movement, the material used for the connecting body, and the like.

By way of example, when the illumination energy coil is preferably made of 18 gauge copper wire and have multiple turns and the connecting body is preferably made of 17-4 PH stainless steel, the voltage signal having between about 1 and about 10 volts, preferably about 1 to about 5 volts, peak-to-peak, may be generated with the vibration frequency of 25 kHz. Those skilled in the art would appreciate that the magnitude of the voltage generated will increase as the number of turns and/or the vibration frequency increase.

Further, in the illustrated embodiment, the voltage may increase as the illumination energy bobbin 126 (and the illumination energy coil 99) is mounted closer to the nodal point on the connecting body 103 than to the distal end where the tip 102 is attached to. The nodal point is where the magnitude of the longitudinal waves on the connecting body is close to zero, and the longitudinal stress is at the maximum, and may in FIG. 6A be the location where the gripping elements 132 are attached to the connecting body 103 (i.e., the indentations 139).

It can be seen in FIGS. 6A and 7 that the illumination energy bobbin 126 has formed thereon a bracket 141 and a seat 142 for mounting the LED 101 thereon. Further, the illumination energy bobbin 126 has formed thereon a flange 143 and a generally cylindrical chamber 144, between which the illumination energy coil 99 is mounted. The generally cylindrical chamber 144 has formed thereon a flange 145. The illumination energy bobbin 126 also includes a ring section 146 attached to the chamber 144. The ring section 146 abuts the flange 121 of the retaining ring 111 when the ultrasonic dental insert 100 has been assembled.

The illumination energy bobbin 126 has formed thereon away from the ring section 146 a tube portion 140 which envelops the portion of the connecting body 103 near the tip 102. In the described embodiment, the fluid enters the illumination energy bobbin 126 through the ring section 146, and exits the illumination energy bobbin 126 through the tube portion 140.

The ultrasonic dental insert of FIG. 6B is substantially the same as the ultrasonic dental insert 100 of FIG. 6A except that the tip 102' has attached to its interface portion 114' a threaded portion 109' for engaging a threaded receiving portion ("engagement portion" or "threaded tap") 119' formed at a distal end of a connecting body 103'. Similar to the ultrasonic dental insert 100, the ultrasonic dental insert of FIG. 6B has a light source 101' (e.g., an LED) mounted on a bobbin 126'. An illumination energy coil 99' is mounted on the bobbin 126' and electrically coupled to the light source 101' such that the illumination energy coil 99' converts the ultrasonic vibrational energy to electrical energy used by the light source 101' for emission. A hand grip 104' at least partly envelops the bobbin 126' and the illumination energy coil 99' in FIG. 6B.

The replaceable tip 102' may be made of metal (e.g., stainless steel) or plastic (e.g., ULTEM®). Since the tip 102' has a very small diameter, it is subject to breakage if too much ultrasonic vibrations are applied to it. On the other hand, if insufficient vibrations are applied, the ultrasonic dental tool may not work effectively. Therefore, the connecting body 103' and the tip 102' maybe designed such that a proper level of vibrations are applied to the tip. Since a plastic tip is more likely to break than the metal tip, a shock absorbing mechanism is used on the connecting body 103' to reduce the shock to the plastic tip.

The connecting body 103' has formed thereon the threaded tap 119' for screwing in the tip 102'. The word "tap" will refer hereinafter to a threaded opening formed at the distal end of the connecting body 103' for engaging the threaded portion 109'. The threaded portion 109' engages a corresponding thread on the inner surface of the threaded tap 119' such that the tip 102' is received by the connecting body 103'.

The connecting body 103' has formed surrounding the threaded tap 119' a pair of grooves 141' and 143' for seating O-rings 140' and 142', respectively. The O-rings absorb shock such that the vibrations "felt" by the tip are reduced (i.e., dampened), thereby reducing the chance of breaking the plastic tip. In other embodiments, the connecting body may have only one or two or more O-rings mounted thereon for such shock absorption purposes. In still other embodiments, the threaded portion may have a diameter that is substantially the same as the diameter of the interface portion, and the diameter of the threaded tap portion may be correspondingly larger to receive the threaded portion.

In the light emitting circuitry of FIG. 8, the light source is an LED 151 connected in series with the illumination energy coil 99. Since the LED 151 emits light in response only to a voltage having single polarity, it emits light only half the time since the illumination energy coil 99 generates an ac voltage signal. However, since the LED 151 switches off and on at ultrasonic frequency (e.g., 25 kHz), such rapid switching of the LED is generally imperceptible to human eyes, and the LED 151 would appear to be continuously on. In other embodiments, the light source 101 may be any other suitable light emitting device such as an incandescent lamp (e.g., halogen light bulb).

In the light emitting circuitry of FIG. 9, a zener diode 150 is connected in parallel to the LED 151. A resistor 152 is connected between the illumination energy coil 99 and the zener diode 150, and a resistor 154 is connected between the zener diode 150 and the LED 151. The zener diode 150 clamps the voltage such that the voltage differential seen by the LED 151 does not rise over a certain predetermined voltage. This way, the brightness of the LED 151 may be kept substantially uniform even if the energy illumination coil 99 begins to generate higher voltage. By way of example, the zener diode 150 may clamp the voltage at 5 volts(V), such that the voltage seen by the LED 151 is no greater than 5V.

In FIG. 10, an LED 161 is connected in an anti-parallel relationship with the LED 151, such that they are connected in parallel but in opposite directions. This way, the LEDs 151 and 161 are alternately turned on in response to the ac voltage generated by the illumination energy coil 99. Since the ac voltage has an ultrasonic frequency (e.g., 25 kHz), the switching on and off of the LEDs 151 and 161 is imperceptible to human eyes, and therefore, both the LEDs 151 and 161 would appear to be on continuously. In other embodiments, the zener diode may be used in parallel with each of the LEDs 151 and 161 in FIG. 9 so as to clamp the voltage for both the LEDs.

As noted, a light source can be of a single LED or multiple LEDs. The multiple LEDs can be arranged in any manner, but preferably in a compact arrangement to minimize the overall size of the light source. Concentric arrays of LEDs may also be used with arrangements, preferably controlled by a microprocessor, such that the areas of illumination can be varied as needed. A light transport apparatus may also be used so that the LEDs can be located inside the connecting body to minimize the size of the protrusion of the tip. The transport apparatus can also include filters or reflectors to vary the size of the area of illumination. Light source as used herein denotes the source of illumination such as the LED(s), or the light transport apparatus, or combinations thereof.

The light source can be a single light source or a plurality of light sources, located substantially proximate to the tip, and connected to receive the voltage signal from the second transducer to generate light or transport light. The plurality light sources can be spaced apart at varying distances from each other, but still preferably located proximate to the tip.

Figure 11:
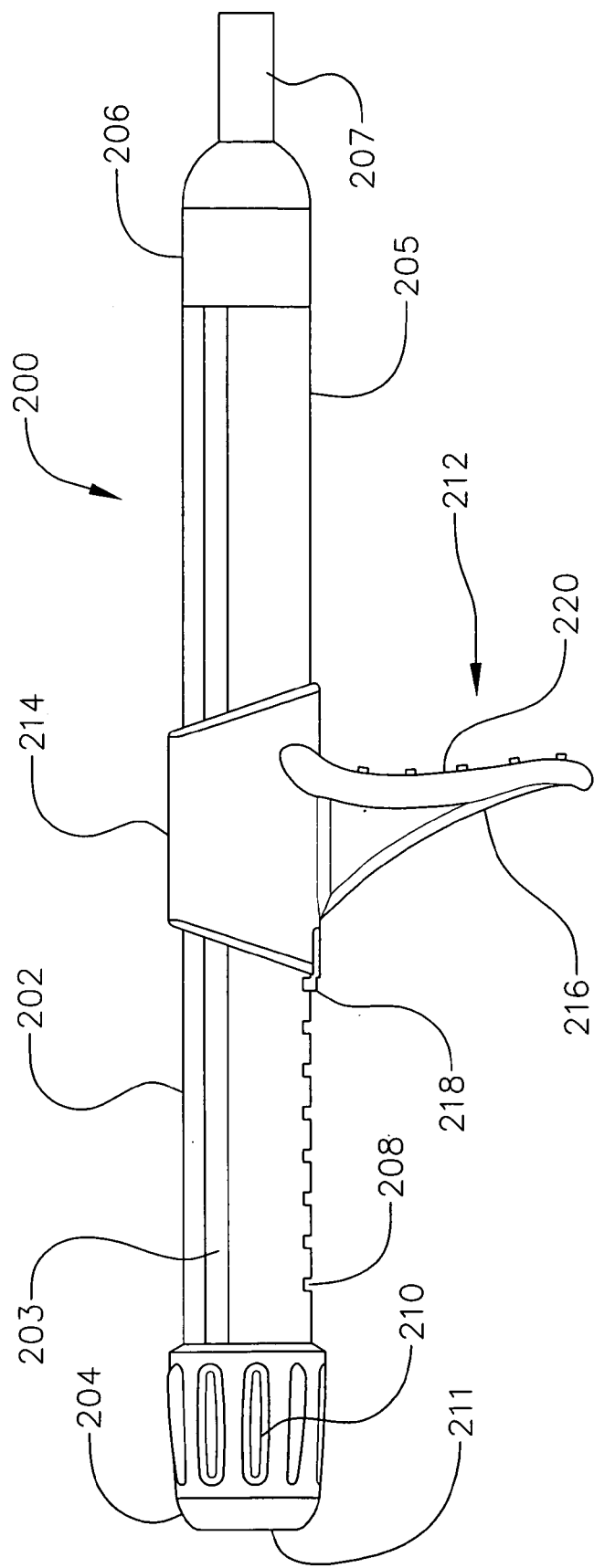
FIG. 11 is a side view of an ultrasonic dental handpiece that can be used with the ultrasonic dental insert of FIG. 2 to form an ultrasonic dental tool.

FIG. 11 illustrates a side view of the handpiece 200 that can receive the insert 100 as seen, for example, in FIG. 1. The handpiece 200 includes a body 202, a rotator head 204 and an interconnect 206. The rotator head 204 located at a distal end of the handpiece 200 is rotatably coupled to the rest of the handpiece 200. When the insert 100 is installed in the handpiece 200, the O-ring 106 is pressure fitted with an inner surface of the rotator head 204, such that the insert 100 rotates together with the rotator head 204.

The interconnect 206 located at a proximal end of the handpiece 200 is coupled to a cable (e.g., the cable 12 of FIG. 1) for providing electrical signals as well as fluid (e.g., water) to the handpiece 200. The interconnect 206 has a strain reliever 207 formed thereon to relieve strain between the interconnect 206 and the cable.

The rotator head 204 has a generally cylindrical shape, a hollow interior, and an opening at each end of the interior, which is used to receive the distal end of the body 202 at one end and a dental insert at the other end. For example, at its distal end, the rotator head 204 has formed thereon an opening 211 for receiving the ultrasonic dental insert 100.

The rotator head 204 has formed around its outer peripheral surface a plurality of indentations 210. Each indentation 210 has an elongated elliptical (or rectangular) shape with its major axis in the direction parallel to the central axis of the handpiece 200. The indentations 210 facilitate grasping of the rotator head 204 by a dental practitioner to rotate it, for example, with respect to the body 202 (e.g., using only one hand). In other embodiments, the rotator head 204 may have a number of protrusions formed thereon instead of the indentations.

The body 202 has formed thereon a pair of grooves 203 that are substantially equidistant from the top and traverse substantially the whole length of the body 202. The grooves 203 are used to mount a hand grip 212 on the handpiece 200. The body 202 has also formed thereon at its bottom near the distal end of the body 202 a plurality of substantially evenly spaced slots 208 that are used to keep the hand grip 212 from moving in the direction of the axis of the handpiece 200. The body 202 has also formed thereon at its bottom near the proximal end a groove 205 that is co-linear to the slots 208. The groove 205 engages the hand grip 212 together with the grooves 203 to keep the hand grip 212 from rotating about the central axis of the handpiece 200. The grooves may not be used in other embodiments.

The hand grip 212 has an engagement portion 214, which has a generally cylindrical shape and a hollow interior. The engagement portion 214 is slipped onto the body 202 similar to a sleeve, and engages the body 202 such that the engagement portion envelops a portion of the body 202. The engagement portion has formed thereon a resilient cantilever portion 218, which is used to engage one of the slots 208 on the body 202. The engagement portion 214 has attached to its bottom surface a handle 216, which is used by a dental practitioner to hold the handpiece 200 during dental procedures. The handle also facilitates rotating of the rotator head 204 using one hand. The handle 216 has formed on its back surface a plurality of indentations or protrusions 220, which are used to facilitate grasping by a dental practitioner.

The handpiece 200 includes at least one coil mounted on a bobbin (shown in FIG. 12) for providing the energy to the stack of nickel plates such that the nickel plates 108 vibrates at an ultrasonic frequency. The coil receives energy from the electrical energy & fluid source 14 through the cable 12 as shown in FIG. 1.

Referring now to FIG. 12, the handpiece 200 further includes a retainer ring 230, which can be made of metal, such as stainless steel. The retainer ring 230 is substantially circular in shape, but does not quite form a complete circle. The retainer ring 230 is flexible (resilient) and works as a spring in that the ends that are not connected together can be brought closer together by applying pressure, but they separate when the pressure is removed.

The rotator head 204 has formed on the inner surface near its proximal end a circular groove 231 that is used to engage the retainer ring 230. The retainer ring 230 is installed in the circular groove 231, for example, by applying pressure on the retainer ring 230 to compress it, and releasing it once the retainer ring 230 has been aligned with the groove 231. Upon installation, the retainer ring 230 is locked to and is fixed with respect to the rotator head 204.

After locking the retainer ring 230 to the groove 231, the rotator head 204 is coupled with the body 202 by receiving the distal end of the body 202 into the rotator head opening at its proximal end. The body 202 has formed at its distal end an engagement portion 209, which has a radius that is smaller than the radius of the rest of the body 202. At a joint between the engagement portion 209 and the rest of the body 202 is formed a substantially circular groove 250 on an outer surface of the engagement portion 209. When the engagement portion 209 is inserted into the rotator head 204, the retainer ring 230 rotatably engages the groove 250 such that the rotator head 204 is rotatably coupled to the body 202. In other embodiments, the retaining ring 230 may be fixedly coupled to the body 202 and rotatably coupled to the rotator head 204.

The body 202 has an inner surface, which defines a hollow cavity 228 formed therethrough, into which a bobbin 236 is received. During a typical ultrasonic dental tool operation, fluid is pumped through the cable and the handpiece 200 to the tip of the insert. The vibrating tip of the insert breaks the fluid stream into a spray. The spray not only keeps the tip cool, but also keeps the surface of the tooth cool and provides protection against tissue damage. The fluid path through the handpiece 200 (through the bobbin 236) needs to be sealed such that no leakage occurs until the fluid stream exits from the insert at the distal end through a fluid delivery channel. In some embodiments, the hollow cavity 228 can have more than one compartments through which air and water can be delivered, respectively. In a preferred embodiment, the compartments are stacked one above the other. The air is delivered via the lower compartment and water is delivered via the upper compartment so that instead of a stream, the air/water mixture becomes a fine mist which can be gentler on the teeth.

The bobbin 236 has a generally cylindrical shape, and formed near its distal end a pair of circumferential grooves 252 and 254. The grooves 252 and 254 engage O-rings 232 and 234, respectively, and are used to prevent fluid from leaking out of the handpiece 200. For example, the O-ring 232 forms a water tight seal with the inner surface of the rotator head 204, while the O-ring 234 forms a water tight seal with the inner surface of the engagement portion 209.

The bobbin 236 has also formed thereon a pair of substantially circular flanges 256 and 258. A long coil 238 is mounted on the bobbin 236 between the flanges 256 and 258. The bobbin 236 has also formed thereon a pair of substantially circular flanges 260 and 262 near its proximal end. A short coil 240 is mounted on the bobbin between the circular flanges 260 and 262. The coils, for example, are made from insulated wires. In other embodiments, the coils may have substantially the same length, or the longer coil may be mounted near the proximal end of the bobbin 236.

Near its proximal end, the bobbin 236 has formed thereon a circular groove 272 for seating an O-ring 242. By seating the O-ring 242 in the groove 272, a water tight seal is formed between the bobbin 236 and the inner surface of the body 202 such that the fluid does not leak from the handpiece 200.

The bobbin 236 has an inner surface, which defines a generally cylindrical cavity for transmitting fluid from the proximal end to the distal end, and has an opening 264 at its proximal end for receiving fluid into the cylindrical cavity. The bobbin 236 has also formed at its proximal end a plurality (e.g., three) of openings 266, which are used to receive plug pins 248 in the bobbin 236. The plug pins 248 are made of electrically conductive material such as copper. The bobbin 236, the body 202, the rotator head 204, the hand grip 212 and the casing for the interconnect 206 are made of a suitable synthetic polymeric material, such as that commonly referred to as "plastic" (e.g., high temperature resin). For example, they may be fabricated using ULTEM®, which is an amorphous thermoplastic polyetherimide available from GE Plastics, as well as others disclosed above.

The bobbin 236 has also formed thereon a plurality of linear grooves 268 that are aligned with and extend from the respective openings 266 to the coils 238 and/or 240. The pins 248 installed, respectively, in the openings 266 and the grooves 268 are soldered and/or otherwise electrically connected to the coils 238 and/or 240, and are used to transmit electrical signals from the electrical energy & fluid and/or air source via the cable through the interconnect 206.

The interconnect 206 has also formed thereon a plurality (e.g., three) of elongated sockets 246 that engage the openings 266, respectively. The elongated sockets 246, for example, are formed on a connector portion 244 of the interconnect 206. The elongated sockets 246 have formed therein electrical contacts for making electrical connections with the plug pins 248, respectively. The electrical contacts are electrically connected at the other end with the wires in the cable, for example, to supply electrical energy to the coils 238 and 240, thereby energizing them.

As noted above, it is common in Europe to use a piezoelectric transducer to generate ultrasonic vibrations for a dental tool. During operation of such a dental tool an electrical signal of an appropriate frequency is applied to a piezoelectric crystal. This electrical signal impresses a voltage across the crystal. In response to this voltage, the crystal expands and/or contracts and the expansion and/or contraction may be used to drive a tool tip.

Figure 13:
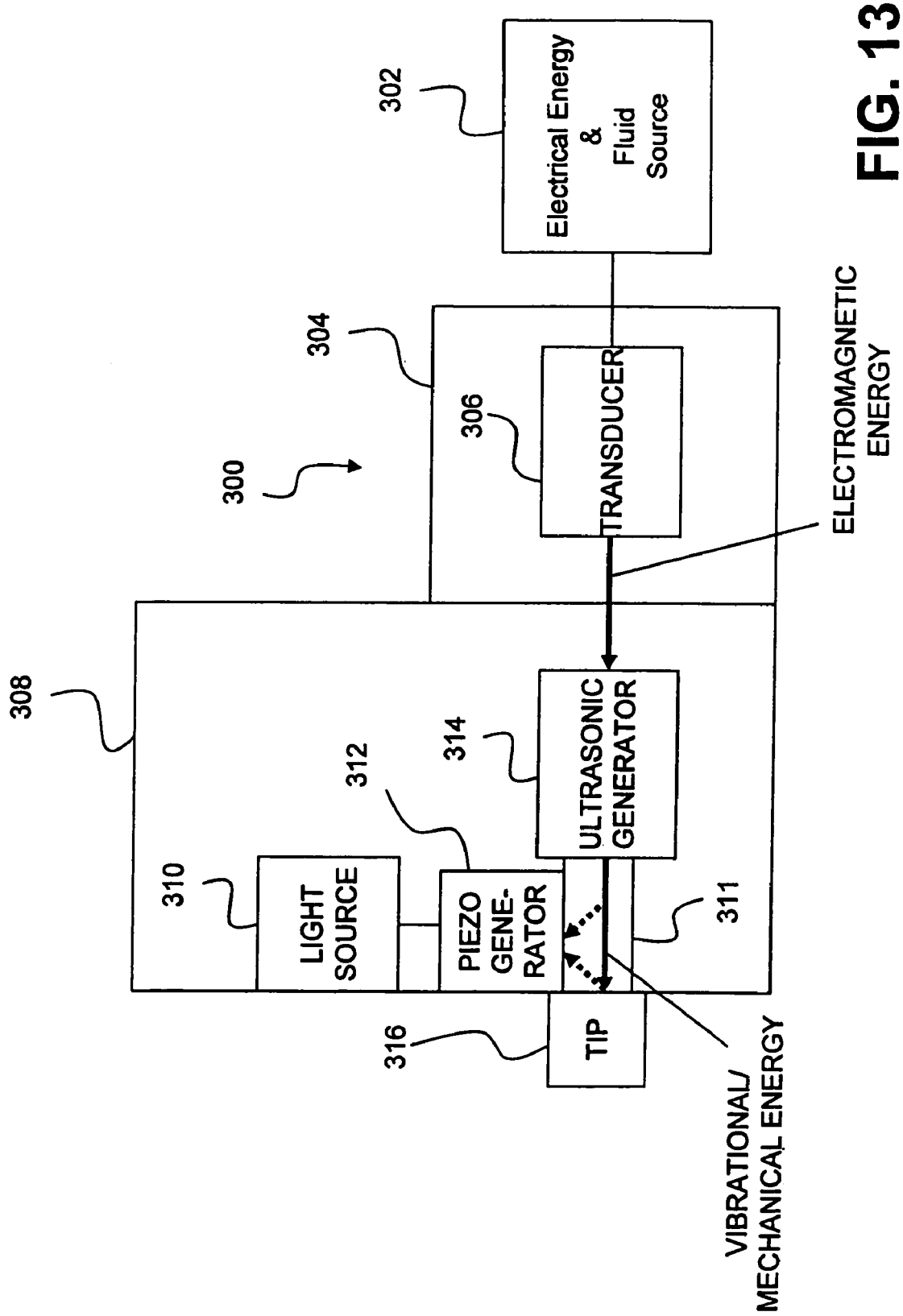
FIG. 13 is a block diagram of another example of an ultrasonic dental unit (or system) including a piezoelectric generator.

As is known by one of skill in the art, the piezoelectric effect is reversible. Applying an appropriate stress to a piezoelectric crystal causes a voltage to appear across the crystal. This voltage, in turn, can be used to drive an electric current through an electrical load, such as a light emitting diode. Accordingly, in one embodiment of the invention shown in FIG. 13, a piezoelectric generator 312 is mechanically coupled to a connecting body adapted to support a tool tip 316 of a dental tool 300.

The dental tool 300 includes a handpiece 304 and a dental insert 308. The handpiece 304 includes a transducer 306, which may be or includes a coil for energizing an ultrasonic generator 314 in the ultrasonic dental insert 308. The handpiece 304 receives electrical energy and fluid and/or gas (e.g., water) from an electrical energy, fluid and/or gas source 302. The handpiece 300, by way of example, may be substantially the same as the handpiece 200 of FIGS. 11 and 12. The dental insert 308 includes a light source 310 coupled to the piezoelectric generator 312. The electrical energy source 302 supplies an electrical signal to the transducer 306. The transducer 306 receives the electrical signal and generates an alternating magnetic field.

In operation, the ultrasonic generator 314 is disposed within the magnetic field and vibrates in response to the alternation of the magnetic field. The vibrations of the ultrasonic generator 314 are mechanically coupled to the tip 316 and to the piezoelectric generator 312. The piezoelectric generator 312 generates an electrical current which is received by the light source 310. The light source 310 may be integrated with the dental insert 308, and may include two or more light sources.

The piezoelectric generator 312 includes a piezoelectric body such as a quartz crystal, a Rochelle salt crystal, or a lead-zirconate-titanate (PZT) ceramic. Vibration of the tool tip 316 and/or a connecting body 311 induces an electrical voltage across the piezoelectric body. The electrical voltage drives a current through the light source 310, such as a light emitting diode, supported on the dental insert 308 of the dental tool 300. According to one aspect of the invention, light from the light source 310 is used to illuminate a work region near the tip 316 of the dental tool 300.

Figure 14:
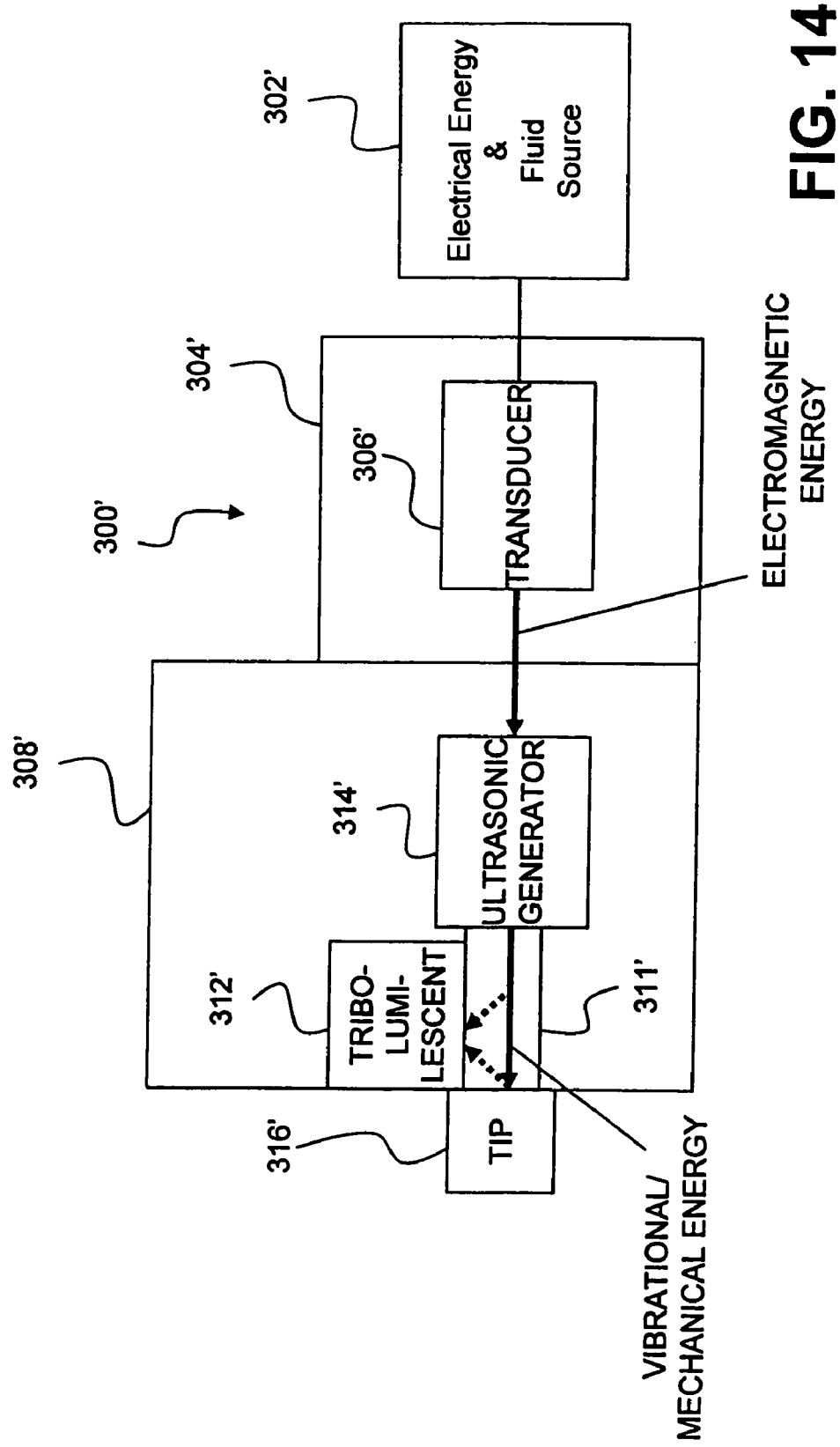
FIG. 14 is a block diagram of another ultrasonic dental unit (or system) including a triboluminescent material.

FIG. 14 illustrates a dental tool 300' having a handpiece 304' and a dental insert 308'. The dental tool 300' is coupled to an electrical energy, fluid and/or gas source 302', and operates in a similar manner as the dental tool 300 of FIG. 13 except that the dental tool insert 308' includes a triboluminescent material 312' preferably located near a tip 316' for providing illumination of the work region. A separate light source may not be needed as the triboluminescent material 312' emits light when stressed/deformed, e.g., by the vibrational energy generated by an ultrasonic generator 314' and transmitted via a connecting body 311'. The energy for the ultrasonic generator 314' is provided by a transducer 306' in the handpiece 304'.

Figure 15:
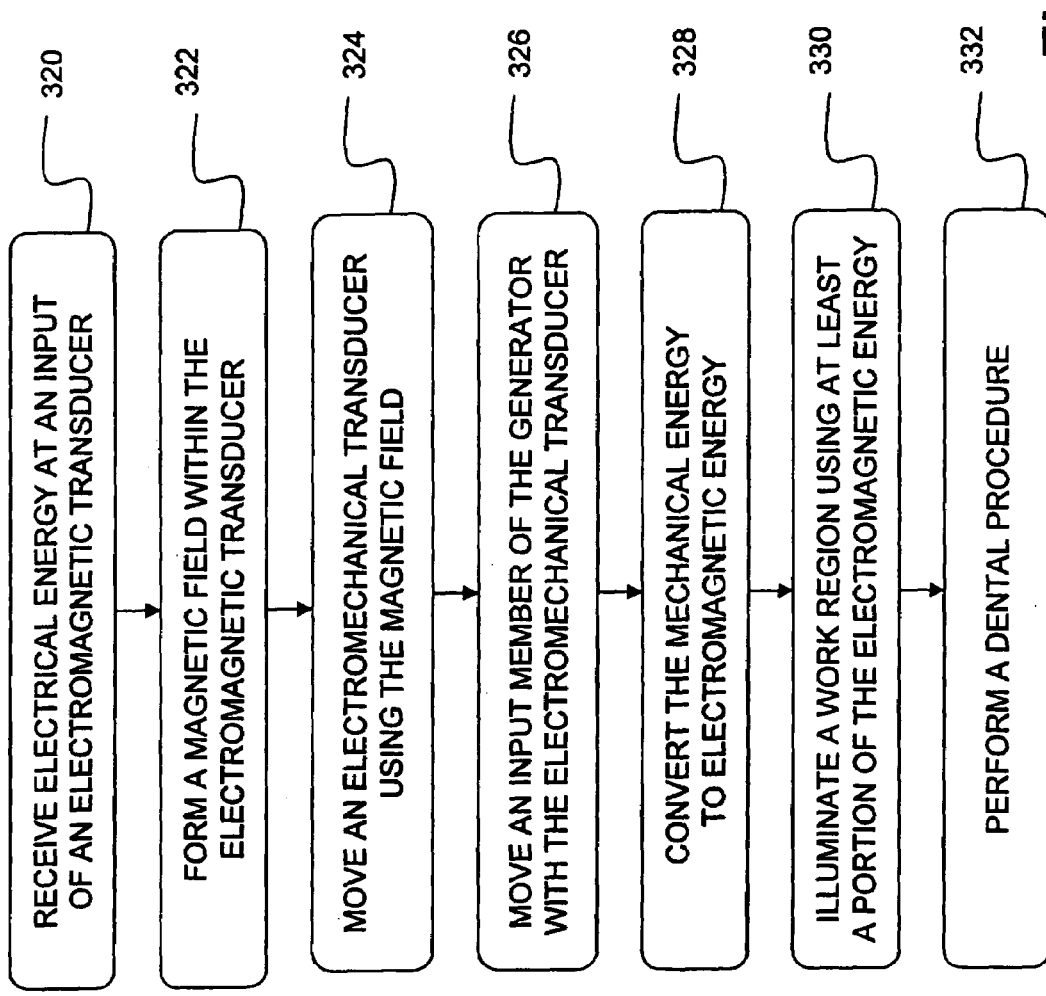
FIG. 15 is a flow diagram illustrating a method of illuminating a work region using the ultrasonic dental tool in exemplary embodiments of the present invention.

FIG. 15 illustrates illuminating a work region such as the mouth of a patient using the ultrasonic dental tool according to exemplary embodiments of the present invention. First, mechanical energy is received at a generator (e.g., the illumination energy coil 99). The generator is mechanically supported by a tool handle (e.g., the handpiece 200). The tool handle is adapted to support an ultrasonic tool tip (e.g., the tip 102). Accordingly, an electrical energy is received at an input of an electromagnetic transducer (e.g., the coil 238)(320). A magnetic field is formed within the electromagnetic transducer (322). The magnetic field moves an electromechanical transducer, e.g., the ultrasonic transducer 108, using the magnetic field (324). By moving an input member, e.g., the connecting body 103, of the generator with the electromechanical transducer, the generator receives the mechanical energy (326). Moving the input member may involve reciprocating the input member at a frequency of from about 25 kHz to about 30 kHz.

The mechanical energy is converted to electromagnetic energy (328). To achieve this, a magnetized member, e.g., the connecting body 103, is moved past an electrical coil, which may include at least one helically-wound electrical conductor. Such moving of the magnetized member may include sliding the magnetized member in a substantially linear motion and/or rotating the magnetized member about a rotational axis. In other embodiments, the mechanical energy may be converted to electromagnetic energy by stressing a piezoelectric member to produce a voltage across the piezoelectric member as discussed above in reference to FIG. 13. In still other embodiments, triboluminescent material may be used to provide the illumination as discussed above in reference to FIG. 14.

At least a portion of the electromagnetic energy thus generated is used to illuminate the work region (330). When converting the mechanical energy to electromagnetic energy to illuminate the work region, an electrical energy may first be generated using the generator. Then the electrical signal is received through an electrical conductor at an input of a light source, which may be an LED or an incandescent lamp (e.g., halogen light bulb). Using the electrical energy, visible light is emitted from the light source. The generator, by way of example, may be disposed within the tool handle.

As shown in FIG. 15, with the illumination, a dental procedure may be performed using the tool handle (332). During the dental procedure, by way of example, a tooth is contacted with a tool tip, which is mechanically coupled to the tool handle, such that a surface of the tooth is disposed within the work region.

It will be appreciated by those of ordinary skill in the art that the present invention can be embodied in other specific forms without departing from the spirit or essential character hereof. The present description is therefore considered in all respects to be illustrative and not restrictive. The scope of the present invention is indicated by the appended claims, and all changes that come within the meaning and range of equivalents thereof are intended to be embraced therein.

I claim:

1. An ultrasonic dental insert comprising:
   a first transducer for generating ultrasonic vibrations;
   a connecting body having a proximal end and a distal end having a tip attached thereto, the proximal end attached to the first transducer so as to receive the ultrasonic vibrations therefrom and to transmit the ultrasonic vibrations toward the tip attached to the distal end;
   a second transducer disposed substantially proximate to the connecting body for generating a voltage signal in response to movement of a portion of the connecting body according to the ultrasonic vibrations; and
   at least one light source substantially proximate to the tip, said at least one light source being connected to and receiving the voltage signal from the second transducer to generate light.

2. The ultrasonic dental insert of claim 1, wherein the second transducer comprises a coil surrounding said portion of the connecting body.

3. The ultrasonic dental insert of claim 2, wherein said at least one light source is an LED connected between a first end of the coil and a second end of the coil.

4. The ultrasonic dental insert of claim 3, further comprising a zener diode connected between the first end of the coil and the second end of the coil, such that the zener diode clamps voltage across the LED to a predetermined value.

5. The ultrasonic dental insert of claim 2, wherein said at least one light source comprises a first LED and a second LED connected in an anti-parallel relationship with one another between a first end of the coil and a second end of the coil, such that the first LED and the second LED are alternately turned on in response to the voltage signal generated by the coil, said voltage signal being an ac voltage signal.

6. The ultrasonic dental insert of claim 2, further comprising a hand grip enveloping at least said portion of the connecting body.

7. The ultrasonic dental insert of claim 6, wherein the coil is at least partially disposed within the hand grip.

8. The ultrasonic dental insert of claim 7, further comprising a bobbin at least partially disposed within the hand grip in a surrounding relationship with said portion of the connecting body, wherein the coil and said at least one light source are mounted on the bobbin.

9. The ultrasonic dental insert of claim 6, wherein the hand grip comprises two hand grip halves that are ultrasonically welded.

10. The ultrasonic dental insert of claim 1, wherein the first transducer comprises a stack of nickel plates.

11. The ultrasonic dental insert of claim 1, wherein the tip is removably attached to the distal end of the connecting body, such that the tip can be replaced by another tip.

12. The ultrasonic dental insert of claim 1, wherein the tip is removably attached to the distal end.

13. The ultrasonic dental insert of claim 12, wherein the removable tip comprises metal, plastic, or a combination thereof, wherein the connecting body has a shock absorbing mechanism located near the tip for reducing a shock experienced by the tip.

14. The ultrasonic dental insert of claim 8, further comprising a retaining ring snapped onto the connecting body, wherein the bobbin is fixedly attached to the retaining ring.

15. The ultrasonic dental insert of claim 6, wherein the hand grip is injection molded over at least said portion of the connecting body.

16. A method of generating light used during dental procedures, comprising:
    generating ultrasonic vibrations using a first transducer attached to a proximal end of a connecting body having the proximal end and a distal end having a tip attached thereto;
    transmitting the ultrasonic vibrations through the connecting body toward the tip attached to the distal end of the connecting body;
    generating a voltage signal using a second transducer disposed substantially proximate to the connecting body in response to movement of a portion of the connecting body according to the ultrasonic vibrations; and
    emitting the light from at least one light source substantially proximate to the tip and connected to the second transducer using the voltage signal.

17. The method of claim 16, wherein said emitting comprises emitting the light from said at least one light source connected to a coil surrounding said portion of the connecting body.

18. The method of claim 17, wherein said emitting comprises emitting the light from an LED connected between a first end of the coil and a second end of the coil.

19. The method of claim 18, further comprising clamping a voltage across the LED to a predetermined value using a zener diode connected between the first end of the coil and the second end of the coil.

20. The method of claim 17, wherein said emitting comprises emitting the light from a first LED and a second LED connected in an anti-parallel relationship with one another between a first end of the coil and a second end of the coil, such that the first LED and the second LED are alternately turned on in response to the voltage signal generated by the coil, said voltage signal being an ac voltage signal.

21. An ultrasonic dental tool comprising:
    an ultrasonic dental insert including:
        a first transducer for generating ultrasonic vibrations;
        a connecting body having a proximal end and a distal end having a tip attached thereto, the proximal end attached to the first transducer so as to receive the ultrasonic vibrations therefrom and to transmit the ultrasonic vibrations toward the tip attached to the distal end;
        a second transducer disposed substantially proximate to the connecting body for generating a voltage signal in response to a movement of a portion of the connecting body according to the ultrasonic vibrations; and
        at least one light source substantially proximate to the tip, said at least one light source being connected to and receiving the voltage signal from the second transducer to generate light; and
    a handpiece for holding the ultrasonic dental insert and for providing electromagnetic energy to the first transducer to generate the ultrasonic vibrations.

22. The ultrasonic dental tool of claim 21, wherein the handpiece has a body and a rotator head rotatably coupled to the body, wherein the ultrasonic dental insert engages the rotator head.

23. The ultrasonic dental tool of claim 22, wherein the handpiece further composes a retainer ring fixedly coupled to one of the body and the rotator head and rotatably coupled to the other of the body and the rotator head, such that the rotator head is rotatably coupled to the body.

24. A method of illuminating a work region comprising:
    receiving mechanical energy at a generator, said generator being mechanically supported by a tool handle, said tool handle being adapted to support an ultrasonic tool tip;
    converting said mechanical energy to electromagnetic energy; and
    illuminating a work region using at least a portion of said electromagnetic energy.

25. A method of illuminating a work region as defined in claim 24 wherein said receiving mechanical energy at a generator comprises:
    receiving electrical energy at an input of an electromagnetic transducer;
    forming a magnetic field within said electromagnetic transducer;
    moving an electromechanical transducer using said magnetic field; and
    moving an input member of said generator with said electromechanical transducer, whereby said generator receives said mechanical energy.

26. A method of illuminating a work region as defined in claim 25 wherein said moving an input member of said generator comprises reciprocating said input member at a frequency of from about 25 kHz to about 30 kHz.

27. A method of illuminating a work region as defined in claim 24 wherein said converting said mechanical energy to electromagnetic energy comprises:
    moving a magnetized member past an electrical coil.

28. A method of illuminating a work region as defined in claim 27 wherein said electrical coil comprises at least one helically-wound electrical conductor.

29. A method of illuminating a work region as defined in claim 27 wherein said moving a magnetized member comprises sliding said magnetized member in a substantially linear motion.

30. A method of illuminating a work region as defined in claim 27 wherein said moving a magnetized member comprises rotating said magnetized member about a rotational axis.

31. A method of illuminating a work region as defined in claim 24 wherein said converting said mechanical energy to electromagnetic energy comprises:
    stressing a piezoelectric member to produce a voltage across said piezoelectric member.

32. A method of illuminating a work region as defined in claim 24 wherein said converting said mechanical energy to electromagnetic energy comprises:
    generating an electrical signal using said generator;
    receiving said electrical signal through an electrical conductor at an input of a light source; and
    emitting visible light from said light source.

33. A method of illuminating a work region as defined in claim 32 wherein said light source is selected from a group consisting of a light emitting diode, and an incandescent lamp.

34. A method of illuminating a work region as defined in claim 24 wherein said generator is disposed within said tool handle.

35. A method of illuminating a work region as defined in claim 24 further comprising:
performing a dental procedure with said tool handle including contacting a tooth with said ultrasonic tool tip, said ultrasonic tool tip being mechanically coupled to said tool handle, such that a surface of said tooth is disposed within said work region.

36. A method of illuminating a work region as defined in claim 24 wherein said converting said mechanical energy to electromagnetic energy comprises:
stressing a triboluminescent material.

37. A method of cleaning a tooth surface comprising:
receiving an ultrasonic signal at a dental tool handpiece;
converting said ultrasonic signal to an ultrasonic motion of a connecting body supporting a dental tool tip;
coupling said ultrasonic motion of said connecting body to an electrical generator; generating electrical current with said electrical generator;
energizing at least one light source with said electrical current;
contacting said dental tool tip to a surface of a tooth; and
illuminating said surface of a tooth adjacent said dental tool tip with said light source.

38. A method of cleaning a tooth surface as defined in claim 37 wherein said converting said ultrasonic signal to ultrasonic motion of a dental tool tip comprises generating a magnetic field using said ultrasonic signal, and applying the magnetic field to a magnetostrictive transducer and responsively oscillating said magnetostrictive transducer at a frequency related to said ultrasonic signal.

39. A method of cleaning a tooth surface as defined in claim 38 wherein said coupling said ultrasonic motion of said dental tool tip to an electrical generator comprises mechanically coupling said magnetostrictive transducer to the connecting body and mechanically coupling said connecting body to said dental tool tip.

40. A method of cleaning a tooth surface as defined in claim 37 wherein said converting said ultrasonic signal to an ultrasonic motion of dental tool tip comprises receiving said ultrasonic signal into a piezoelectric transducer and responsively oscillating an output member of said piezoelectric transducer at a frequency related to said ultrasonic signal.

41. A method of cleaning a tooth surface as defined in claim 40 wherein said coupling said ultrasonic motion of said dental tool tip to an electrical generator comprises mechanically coupling said output member of said piezoelectric transducer to the connecting body and mechanically coupling said connecting body to said dental tool tip.

42. A method of cleaning a tooth surface as defined in claim 40 wherein said generating an electrical current with said electrical generator comprises cyclically compressing and releasing a piezoelectric body.

43. A method of cleaning a tooth surface as defined in claim 42 wherein said piezoelectric body comprises a common piezoelectric body with a piezoelectric body of said piezoelectric transducer.

44. A method of cleaning a tooth surface as defined in claim 37 wherein said generating an electrical current with said electrical generator comprises:
oscillating a magnetized member adjacent a helical arrangement of electrical conductors.

45. A method of cleaning a tooth surface as defined in claim 37 wherein said generating an electrical current with said electrical generator comprises cyclically compressing and releasing a piezoelectric body.

46. A method of cleaning a tooth surface as defined in claim 45 wherein said piezoelectric body comprises a quartz crystal.

47. A method of cleaning a tooth surface as defined in claim 45 wherein said piezoelectric body comprises a Rochelle salt crystal.

48. A method of cleaning a tooth surface as defined in claim 45 wherein said piezoelectric body comprises a PZT ceramic.

49. A dental tool comprising:
means for applying mechanical energy to a support member;
means for applying a first portion of said mechanical energy to a work surface;
means for converting a second portion of said mechanical energy to electrical energy; and
means for converting at least a portion of said electrical energy to visible light.

50. A dental tool as defined in claim 49, wherein said means for applying mechanical energy to a support member comprises a magnetostrictive ultrasonic transducer.

51. A dental tool as defined in claim 49 wherein said means for applying mechanical energy to a support member comprises a piezoelectric ultrasonic transducer.

52. A dental tool as defined in claim 49 wherein said means for converting a second portion of said mechanical energy to electrical energy comprises an electromagnetic generator.

53. A dental tool as defined in claim 49 wherein said means for converting a second portion of said mechanical energy to electrical energy comprises a piezoelectric generator.

54. A dental tool as defined in claim 49 wherein said means for converting at least a portion of said electrical energy to visible light comprises a light emitting diode.

55. A dental tool as defined in claim 49 wherein said means for converting at least a portion of said electrical energy to visible light comprises an incandescent lamp.

56. A dental tool as defined in claim 55 wherein said incandescent lamp comprises a halogen light bulb.

57. A dental tool as defined in claim 49 wherein said means for applying a first portion of said mechanical energy to a work surface comprises a dental tool tip.

58. An ultrasonic dental insert comprising:
a motor;
a work tip;
a coupling member disposed between said motor and said work tip, said coupling member being adapted to receive mechanical energy from said motor;
an electrical generator, said electrical generator being mechanically coupled to said coupling member, said electrical generator being adapted to receive a portion of said mechanical energy from said coupling member;
an electrical conductor having a first end, said first end being electrically coupled to said electrical generator; and
at least one light source, said light source having an electrical input, said electrical input being electrically coupled to a second end of said electrical conductor.

59. The ultrasonic dental insert as defined in claim 58 wherein said at least one light source comprises a light emitting diode.

\* \* \* \* \*

UNITED STATES PATENT AND TRADEMARK OFFICE
CERTIFICATE OF CORRECTION

PATENT NO. : 7,104,794 B2  Page 1 of 1
APPLICATION NO. : 10/879554
DATED : September 12, 2006
INVENTOR(S) : Levy It is certified that error appears in the above-identified patent and that said Letters Patent is hereby corrected as shown below:

In the Claims

Column 16, line 2, Claim 23     Delete "composes",
                                Insert --comprises--

Signed and Sealed this

Twenty-sixth Day of June, 2007

JON W. DUDAS
*Director of the United States Patent and Trademark Office*